(12) United States Patent
Wang

(10) Patent No.: US 7,157,227 B2
(45) Date of Patent: Jan. 2, 2007

(54) MICROARRAYS TO SCREEN REGULATORY GENES

(75) Inventor: Eugenia Wang, Prospect, KY (US)

(73) Assignee: University of Louisville Research Foundation, Louisville, KY (US)

( * ) Notice: Subject to any disclaimer, the term of this patent is extended or adjusted under 35 U.S.C. 154(b) by 848 days.

(21) Appl. No.: 09/820,531

(22) Filed: Mar. 29, 2001

(65) Prior Publication Data

US 2002/0009736 A1   Jan. 24, 2002

Related U.S. Application Data

(60) Provisional application No. 60/193,888, filed on Mar. 31, 2000.

(51) Int. Cl.
  C12Q 1/68   (2006.01)
  C07H 21/02  (2006.01)
  C07H 21/04  (2006.01)

(52) U.S. Cl. ............... 435/6; 536/23.1; 536/24.3

(58) Field of Classification Search ............ 435/6, 435/91.1, 91.2, 183, 287.2; 436/94; 530/350; 536/23.1, 24.3, 24.33
See application file for complete search history.

(56) References Cited

U.S. PATENT DOCUMENTS

| | | | |
|---|---|---|---|
| 5,474,796 A * | 12/1995 | Brennan | |
| 5,605,662 A * | 2/1997 | Heller et al. | |
| 6,013,437 A | 1/2000 | Luria et al. | |
| 6,028,189 A * | 2/2000 | Blanchard | |
| 6,136,541 A | 10/2000 | Gulati | |
| 6,329,140 B1 * | 12/2001 | Lockhart et al. | |
| 6,524,800 B1 * | 2/2003 | Lockhart et al. | |
| 2005/0054597 A1 * | 3/2005 | Furusawa | 514/44 |

FOREIGN PATENT DOCUMENTS

| WO | WO9525116 | * | 9/1995 |
| WO | WO9535505 | * | 12/1995 |

OTHER PUBLICATIONS

DeRisi et al., Nature Genetics 14 (4): 457-460 (Dec. 1996).*
Heller et al., PNAS 94 : 2150-2155 (Mar. 1977).*
Lockhart et al., Nature 405 :827-836 (Jun. 15, 2000).*
Schena et al., PNAS 93 : 10,614-10,619 (1996).*
Alberts et al. "Molecular Biology of the Cell", 3rd Edition. Published by Garland Publishing, Inc. (1994) pp. 223-226.*
Bowtell, "Options available—from start to finish—for obtaining expression data by microarray," Nat Genet 21(1 Suppl):25-32 (1999).
Ramsay, "DNA chips: state-of-the art," Nat Biotechnol 16(1):40-44 (1998).
Wang, et al., "Large-scale identification, mapping, and genotyping of single-nucleotide polymorphisms in the human genome," Science 280(5366):1077-1082 (1998).

* cited by examiner

Primary Examiner—Ethan Whisenant
(74) Attorney, Agent, or Firm—Stites & Harbison PLLC

(57) ABSTRACT

Microarray technology allows the multiple parallel processing of information generated from matrices of huge numbers of loci on a solid substrate, which is useful in the gathering of gene signatures defining specific biological states. An approach has been developed to facilitate this process wherein genes of the same regulatory modality are selected. The transcriptional regulation of these genes is related to the same control element. Primers specific for the regulatory genes are selected, based on minimum cross-reactivity with other genes, using known gene data banks. PCR products of selected regions of known genes either binding to this sequence or whose expression is dependent on this binding, as well as genes interacting with the regulatable genes and control genes, referred to as "amplicons" or "gene cDNA fragments" of between about 450 and 1000 nucleotide bases in length, are obtained from a total RNA pool. These amplicons are arrayed on a nylon membrane or other appropriate microchip susbstrate, which is then used as a regulatory gene-specific microarray that is hybridized with sample. Sample will typically be the mRNA obtained from cells associated with a particular state (examples include age or exposure to conditions such as outspace, low gravity), disease (such as cancer or an infection), or disorder (such as a genetic defect or trauma). The transcriptionally regulated profile of regulatory gene-related genes specific to a given cultured cell sample is then determined using a software based analysis of the amount of hybridization which is detected. This information is useful in determining drug targets, markers associated with the disease state (either the presence or absence, or the extent of the disease), or the response of the disease state to drugs or other treatments.

19 Claims, 2 Drawing Sheets

MICROARRAYS TO SCREEN REGULATORY GENES

This application claims priority to U.S. Ser. No. 60/193,888 filed Mar. 31, 2000.

The United States government has certain rights in this invention by virtue of grants to Eugenia Wang from the National Institute on Aging (AG09278) and from the Defense Advance Research Project Agency (DARPA) of the Department of Defense of the United States of America.

BACKGROUND OF THE INVENTION

With the advent of the Human Genome Project, one is confronted with voluminous information demonstrating that biological systems may be controlled by hundreds of genes working in concert. A single glance at the ever-increasing number of genes involved in signal transduction makes one wonder just how many genes are needed to choreograph the symphonic dance of implementing a signal, from the receptor-ligand binding to the nuclear response of transcriptional activation. During the 1980's and early 1990's, biologists were busy dissecting single genes' functions from the reductionist point of view. This approach, while thorough in its exact methodological analysis of genetic impact, lacks the expanded vision of how each particular single gene functions in the context of many sister genes or partners, to accomplish a biological task. Thus, it is not surprising that the technology of high-throughput gene screening is emerging rapidly, in the attempt to identify tens or hundreds of genes whose changes, viewed in composite genetic signatures, define a particular physiological state. This gene signature approach, complemented by single gene analysis, provides a vertical, in-depth analysis of an individual gene's function, as well as the comprehensive picture of the pattern of gene expression in which the particular gene functions. The notion of genetic signature can be further generalized to address the question of inter-individual variance, by comparing individuals from cohorts of hundreds or thousands.

The unfathomable task of comparing several dozens of single nucleotide polymorphisms (SnP) in a hundred people can now be approached easily by DNA biochip technology (Wang, et al. Science 280: 1077–1082 (1998)). For example, a p53 DNA chip is used popularly for the identification and gene screening of unique cancer risks, to discover new SnPs as well as screening known SnPs. Either task needs a fast, multiplex approach requiring data entry on the scale of hundreds and thousands, a demand that can only be met by high-throughput technology. The presently available microarray biochip technology is certainly the method of choice to solve the problem of complexity, and the previously impossible task of defining a genetic signature for a unique person in a cohort with accuracy and speed that are impossible by the conventional diagnostic approach. Therefore, from bench-side researchers to bedside physicians, there is intense interest in the technology of microarray analysis, for screening or identifying tens or hundreds of genes related to disease or normal states of a given person or biological system.

cDNA and oligonucleotide microarrays are becoming an increasingly powerful technique for investigating gene expression patterns. In spite of the fast progress in this field, some limitations of the technique persist. One of the major obstacles is the requirement for a large amount of mRNA. Another problem with existing microarray systems is data mining; since information on expression of tens of thousands genes is absolutely vital to estimate the functions of new genes, but of little use in determining the expression profile of only a subset of genes, especially when analyzing specific gene expression associated with a particular physiological condition such as age, disease or a disorder.

It is therefore an object of the present invention to provide a method and materials for the rapid analysis of genetic information based on a common regulatory gene feature.

It is a further object of the present invention to provide a method and materials for sensitive and quick analysis of genetic information present in very small quantities associated with a particular physiological or disease state or condition.

SUMMARY OF THE INVENTION

Microarray technology allows the multiple parallel processing of information generated from matrices of huge numbers of loci on a solid substrate, which is useful in the gathering of gene signatures defining specific biological states. An approach has been developed to facilitate this process wherein genes of the same regulatory modality are selected. The transcriptional regulation of these genes is related to the same control element. Primers specific for the regulatory genes are selected, based on minimum cross-reactivity with other genes, using known gene data banks. PCR products of selected regions of known genes either binding to this sequence or whose expression is dependent on this binding, as well as genes interacting with the regulatable genes and control genes, referred to as "amplicons" or "gene cDNA fragments" of between about 450 and 1000 nucleotide bases in length, are obtained from a total RNA pool. These amplicons are arrayed on a nylon membrane or other appropriate microchip susbstrate, which is then used as a regulatory gene-specific microarray that is hybridized with sample. Sample will typically be the mRNA obtained from cells associated with a particular state (examples include age or exposure to conditions such as outspace, low gravity), disease (such as cancer or an infection), or disorder (such as a genetic defect or trauma). The transcriptionally regulated profile of regulatory gene-related genes specific to a given cultured cell sample is then determined using a software based analysis of the amount of hybridization which is detected. This information is useful in determining drug targets, markers associated with the disease state (either the presence or absence, or the extent of the disease), or the response of the disease state to drugs or other treatments.

DETAILED DESCRIPTION OF THE INVENTION

Figure 1:
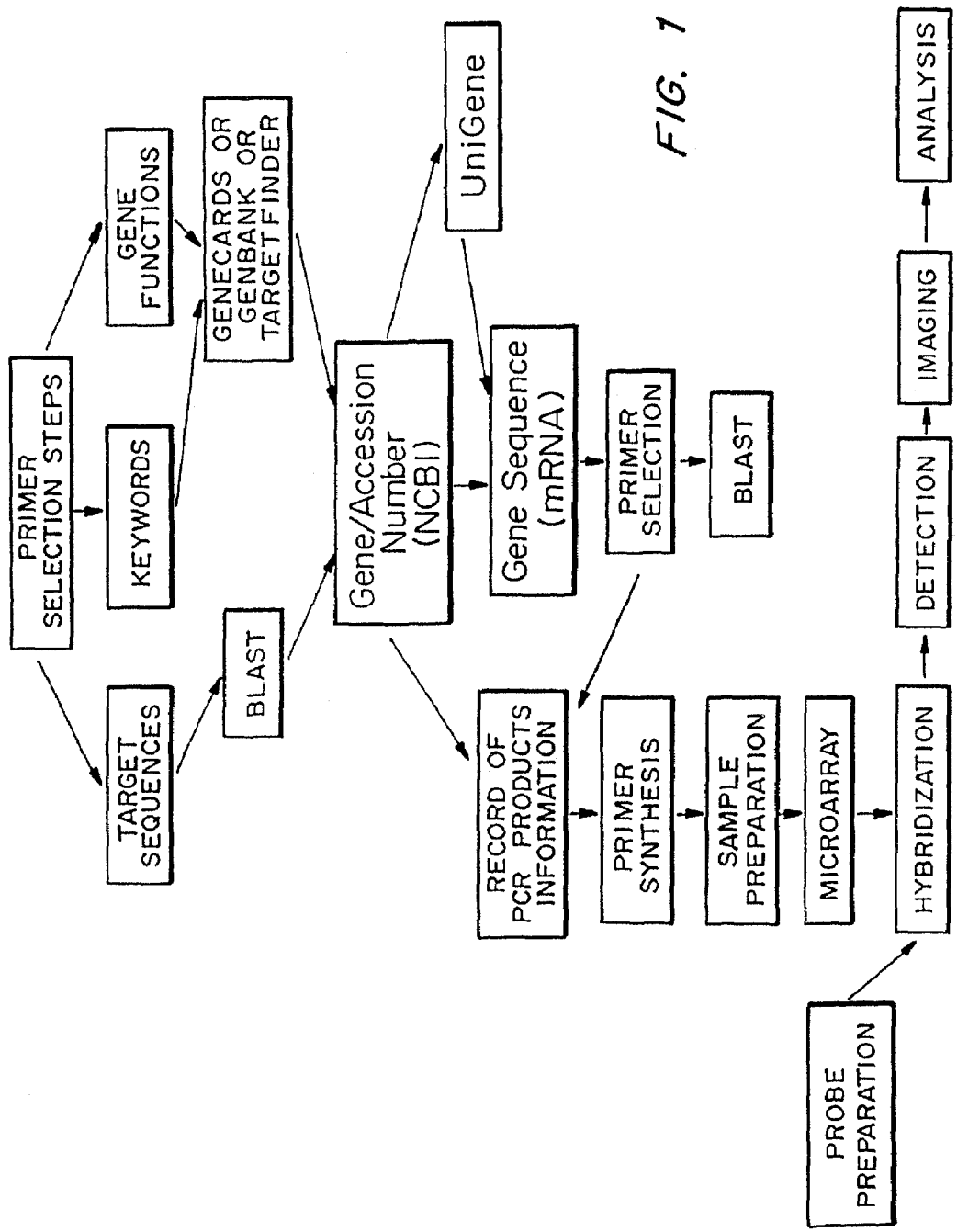
FIG. 1 is a schematic of the process described herein for making and using microarrays selected based on the presence of a common regulatory element.

Every gene consists of two important sequence elements: (a) coding sequence elements, specific nucleotide sequences that spell out what the eventual gene product will be; and (b) regulatory sequences, located outside the coding sequence regions, and in general determining the activation or deactivation of the expression of a specific gene. In general, the regulatory region is composed of specific sequences which allow binding of other proteins to this DNA nucleotide element; this binding action then determines when the designated gene is activated for its transcription, or deactivated for its transcription. Genes involved in activation are called enhancers or promoters, while genes involved in de-activation are called repressors or suppressors. For each enhancer or suppressor, there are a family of other co-factors whose action can either help or compete with the enhancing or suppressing function. Therefore, each enhancer or suppressor could be partnered with several other gene products to form an enhancer-activation complex, or suppressor-function complex, and the two types of complexes can be simultaneously competing for binding with the regulatory region. In any given physiological condition, a regulatory region can be involved with a series of at least two competing complexes, each composed of several co-factors. Furthermore, a specific regulatory sequence can belong to a group of genes sharing the same functional activation.

Therefore, a regulatory-sequence based gene microarray (or "chip") is composed of:
(a) genes whose non-coding region contains the same defined nucleotide bases for enhancers or repressors to bind to; and
(b) genes whose protein products can bind to designated regulatory sequences. There are many examples of such regulation occurring in cells, and promotion of a specific cellular event usually requires the concerted and coordinated activation of a group of genes. Most notably, activating any cell signaling pathway in general requires a series of regulatory genes to be activated. A famous example, cell proliferation, may involve the insulin-response element, the E2F transcription factor, and RAS-responsive element binding proteins. Therefore, design of regulatory-sequence based gene microarrays is a rationale strategy in gene screening, allowing the results gained to immediately be applied as a reflection of a regulatory pathway, rather than random hit-or-miss gene screening.

For analysis of the microarray, it is preferable that the microarray also include "housekeeping" genes, or genes that are not affected by the same regulatory sequences, whose level of expression remains constant in the particular disease, state or disorder to be examined, so that the amount of expression can serve as a background level to be used for comparative purposes, to determine if a particular gene is turned on or off in that disease, disorder or other state to be examined.

These techniques are in contrast to the currently available DNA microarray technology which is based on screening with gene sequences based on the coding sequences of thousands of genes, many of which may only be "ESTs" of unknown function. The results obtained from gene screening provide only a general sketch of which gene expressions are gained or lost in a specific physiological condition. Most of them group genes by their functional capability, such as cell proliferation, cell cycle apoptosis, of DNA repair, whereas the techniques described herein groups genes according to their regulatory modalities. The technology described herein is based on designing a specific subset of genes whose expressions are regulated by the same regulatory mode, i.e. the activation of gene expression based on the activation or de-activation of defined DNA sequences.

In the preferred embodiment, each gene chip is composed of a few dozen to a couple of hundred genes per gene chip platform. The gene screening task involves the use of a selection of a few gene microarrays from a selected list. Therefore, a gene-screening task of a few thousand genes becomes in our case screening a dozen gene microarrays each composed of perhaps 100 genes. This divide-and-conquer approach provides the versatility which renders the gene screening attempt user-friendly, while the current technology of each platform being composed of thousands of genes allows no flexibility of focusing on screening a selected gene family of interest.

This approach solves the following problems of the current technology of gene chip screening tasks:

Ease of datamining: The current technology of gene screening using large numbers of genes grouped by functional capability generates a tremendous amount of data, which produces subsequent problems in data evaluation. For example, when a known chip bearing the coding regions of 10,000 genes is screened, it provides perhaps a few hundred genes whose expressions may display significant gain or loss for a given physiological state. Sorting out these few hundred genes into a hierarchy of respective importance in terms of upstream or downstream function is a very tedious task, requiring a lot of manpower and computing time. Using cassettes of gene microarrays manufactured according to regulatory modality avoids this problem, i.e., positive or negative changes of gene expression on a given five or six DNA microarrays provides immediate assessment of which pathways are involved, since these microarrays are designed according to regulatory pathways. Furthermore, the quantitative levels of gain or loss of gene expression for a given gene provide self-evident implications of the hierarchic order of genes, with regard to the separation of a master gene switch versus pedestrian gene changes.

Reliability of data generation: The fact that the genes are grouped into subsets according to regulatory modality for gene expression provides a platform for gene microarrays of similar abundance of gene expression. In general, all gene expressions in a cell can be grouped into three categories: (a) genes whose expression is abundant, such as actin, tubulin, and EF-1alpha; (b) genes whose expression is of intermediate level, such as calmodulin, MAPkinase, and others; and (c) minor genes whose expression is of low abundance, such as Tumor necrosis factor, c-myc, p21, etc. When genes of widely varying abundance are used together on the same platform, the end result is that signals for abundant genes are revealed first. If the abundant genes are positioned on the microarray adjacent to minor genes, the latter are overshadowed. The photographic process of developing these gene-screening platforms will create either regions of overshadowed, unreliable data, or regions containing information that can never be developed because of the overpowering effect of nearby abundant genes. This scenario is one of the problems of using the current wholesale approach to gene chip analysis. This problem is eliminated by selecting of the genes on the microarray from the category of minor genes, whose expression is of analogously low level of intensity, therefore bypassing this problem of the wholesale gene chip approach.

Flexible and versatile strategy for the gene screening task: In general, gene screening may be categorized into two types: the first type, termed herein as wholesale gene screening, and the second type, termed herein as segmental gene screening. The first type can be viewed as the ultimate fishing expedition, with no specific goals or aims in the gene identification process. In this case, the approach is rewarded by a return of hundreds of genes identified as gained or lost in a given physiological state. This result tends to be a random hit-or-miss approach, and the investigators quickly realize that they need follow-up experiments to sort out all the information to make it useful. This second type of approach is intended to focus on specific groups of genes, perhaps hundreds, and then determine their gain or loss based on rational subcategories of functions or regulatory modality.

Microarrays

Although described herein generally with regard to nylon membranes or glass or silica supports, microarrays can be prepared using any standard technique to make microarrays on a solid support. Robotic systems which pipet nano to picomolar amounts of gene products onto the support are commercially available or can be built using commercially available materials. Websites are provided herein which include detailed information on methods and sources of materials for making microarrays.

Information Resources

There are several DNA microchip technology reviews in the literature (Bowtell, D. D. L. Nature Genetics Supplement 21:25–32 (1999); Constantine and Herrington, Life Science News 1:11–13 (1998); Ramsay, G. Nature Biotechnology 16:40–44 (1998)), and several good web sties detailing the apparatus and protocols used by other laboratories. Table 1 lists several organizations and entities, including highly active laboratories in DNA microchip technology, as well as several sources of robotics systems and equipment imaging software and systems and vendors of robotic components, each of which have an associated web site containing useful information.

The Microarrayer

A turnkey microarrayer can be purchased, with an enclosure for temperature, humidity and air quality control; a system such as the GeneMachines™ OmniGrid (San Carlos, Calif.) would be sufficient. Alternatively, to save on the cost of a robotic system, a microarrayer can be built in the laboratory. The Brown Laboratory web site, for example, gives full details for component specifications, mechanical drawings for machined parts, a list of vendors, an assembly guide, and free microarrayer software.

Operation of the Tips, XYZ Motion Control, and Computer Program

The robotic gantry of a typical printing tip microarryer is composed of 3 individual assemblies of linear robotic tables, and motors driven by 3 corresponding amplifiers which are coupled to a motion controller in the driving computer. All of this forms the appropriate 3-axis motion control system (i.e.: X, Y and Z axes) for microarraying. The three perpendicular axes allow for sampling, printing and washing with the components of the microarryer system.

Printing Substrate and Samples

In terms of a printing substrate for producing the microarrays, poly-L-lysine-coated glass slides seem to work best to immobilize the printed DNA. Nylon hybridization membranes can also be used as the printing substrate, and allow for a much easier immobilization protocol, as well as better visualization if a colorimetric method is used for hybridization detection.

To contain the samples, conical 96-well microplates work well by localizing small volumes of sample in the wells. When printing many different samples, 384-well microplates are best due to their higher capacity and low storage volume and the smaller sample sizes ($\leq 10$ μl) can be used readily. During storage, sample plates should be covered with an adhesive-backed plastic seal, to prevent sample loss by evaporation.

Sample Preparation

Samples prepared for printing are loaded into 384-well microplates, 10 μl aliquots per well. These samples can be used for up to 8 to 10 printing runs, with proper storage. In printing arrays with the ArrayIt™ printing tips on the GeneMachines™ OmniGrid microarrayer, it is possible to print several thousand spots onto one chip either in one array or duplicate arrays on one chip. The printing tip delivery volume is approximately 1 nl per spot with a spot diameter of approximately 100 μm. Therefore, depending upon the surface area of the substrate being used as the chip and the number of tips used for printing, several large arrays are possible with close spacing (less than 100 um) for up to 100 microarrays per run. For typical experiments in this laboratory, arrays are printed in duplicate 20×20 arrays per chip with a spot spacing of 250 μm using between 20 to 30 microarrays per run.

To extend the lifetime of the samples, after printing, the microtiter plates are sealed with adhesive-backed plastic covers in addition to the microplate lids. Furthermore, before using the stored samples again, the microplates are centrifuged to gather any condensate in the wells, and to localize the sample fluids at the bottom of each well.

Array Analyzer/Imaging System

Depending upon the selected approach to hybridization analysis of the printed microarrays, a system fitted onto an existing microscope, a microarray scanner or confocal laser scanner may be purchased, or a confocal laser scanner may be built.

The system used to compile the digital microarray images is built around an Olympus BH-2 upright light microscope, fitted with a Sony color CCD camera, an Applied Scientific Instrumentation (Eugene, Oreg.) X-Y scanning stage, and a fiber optic ring illuminator from Edmund Scientific Co. (Barrington, N.J.). EMPIX Imaging, Inc. (Mississauga, ON) assembled the system for compiling microarray images, containing a 24 bit frame grabber; it is installed in a 450 MHz P3 PC equipped with 512 Mb RAM and a 19" SVGA monitor, where the image acquisition and system control are governed under the Windows 98 operating system by Northern Eclipse™ imaging software. A 3COM™ 10/100 Base TX network card installed in the computer links the imaging computer to a small LAN (Lynksys, Irvine, Calif.), containing a color laser printer and two other computers used for image analysis and data storage.

The size of the arrays and individual spots dictates the use of low power objectives (either 2.5× or 4×) and the X-Y scanning stage to capture the image of the entire array.

Many of our microarray experiments are done using nylon membranes (Hybond-N) as the printing substrate. Probes are labeled with DIG-dUTP in a reverse transcription reaction; target/probe hybridization is detected with anti-DIG-coupled alkaline phosphatase, and a subsequent reaction of the alkaline phosphatase with an NBT/BCIP stain/substrate. This method requires the ring illuminator to distinguish artifacts from array spots on the stained hybridization membranes. Otherwise, if poly-L-lysine coated glass slides are used as the microarray printing substrate, illumination of the microarray specimen is carried out normally.

Image Quantitation

When the microarray digital imaging routine is completed, the compiled montage can be transferred by way of the network to the computer stations devoted to image analysis and data storage. The microarray images are created as TIFF files; before quantitation can begin, the raw digital images are filtered to bear only the microarray signal data, aligned in Adobe PhotoShop™ software, and then transferred to the GeneAnalyzer microarray analysis software. GeneAnalyzer removes the background, and the reduced digital microarray images are passed through an image location routine to optimally localize the spots of the microarray image. When the GeneAnalyzer software has "grabbed" the individual spots of the reduced digital microarray image, the program can proceed to quantitate the density of the individual spots. Each spot on the microarray is then regarded as an individual signal, and its intensity serves as the foundation of the data needed to reflect the hybridization reaction. After comparison with appropriate positive and negative controls for nonspecific reactions, true signal value is subtracted from noise to produce the desired information on each hybridization reaction.

The microarray spot density data are transferred into an analysis routine in the mathematical analysis software, MATLAB, for graphical representation of all data; the density values, as well as the respective calculated values, of all digitized microarray data are tabulated in a Microsoft Excel™ spreadsheet. A full record of the progression of images, tabulated data and all graphical representations can immediately be printed to complete the microarray experiment analysis.

TABLE 1

Informative web sites for DNA microarray technology

| DNA microarray technology web sites | URL |
| --- | --- |
| Automation and Miniaturization in Genome Analysis, Max Plank Institute for Molecular Genetics | http ://www.mpimg-berlin-dahlem.mpg.de/~autom/autom.htm |
| Department of Molecular Biotechnology, University of Washington | http://chroma.mbt.washington.edu/mod_www/ |
| Functional Genomics Group, Albert Einstein College of Medicine | http://sequence.aecom.yu.edu/bioinf/funcgenomic.html |
| Genomics Group, Children's Hospital of Philadelphia | http://w95vcl.neuro.chop.edu/vcheunng |
| Laboratory of Cancer Genetics, National Human Genome Research Institute | http://www.nhgri.nih.gov/Intramural_research/Lab_cancer/ |
| Joint Genome Institute, Lawrence Livermore National Laboratory | http ://llnl.gov/automation-robotics/poster.1.html |
| Pat Brown Laboratory, Stanford University | http://cmgm.stanford.edu/pbrown |
| Stanford DNA sequence and Technology Center Stanford University | http ://-scquence.stanford.edu/group/techdev/ |

| Microarrayers, imaging systems and scanners | |
| --- | --- |
| Applied Scientific Instrumentation, Inc. | http://www.ASIimaging.com/ |
| Axon Instruments, Inc. | http://axon.com/GN_Genomics.html |
| Beecher Instruments | http://www.beecherinstruments.com/ |
| BioDiscovery, Inc. | http://www.biodiscovery.com/ |
| BioRobotics, Ltd. | http://www.biorobotics.coml |
| Empix Imaging, Inc. | http://www.empix.com/ |
| GeneMachines, Genomic Instrumentation Services, Inc. | http://www.genemachines.com/ |
| General Microarray Information | http://www.microarray.org/ |

TABLE 1-continued

Informative web sites for DNA microarray technology

| | |
| --- | --- |
| General Scanning, Inc. | http://www.genscan.com/ |
| Genetic MicroSystems, Inc. | http://www.geneticmicro.com/ |
| Genometrix, Inc. | http://www.genometrix.com/ |
| Genomic Solutions | http://www.genomicsolutions.com/ |
| Imaging Research, Inc. | http://www.imagingresearch.com/ |
| Intelligent Automation | http://www.ias.com |
| Molecular Dynamics, Inc. | http://www.mdyn.comlarrays/arraywhat.htm |
| Radius Biosciences | http://www.ultranet.com/~radius |
| Research Genetics | http://www.resgen.com |
| ScanAlyze software | http://bronzino.stanford.edu/ScanAlyze/ |
| Telechem International, Inc. | http ://www.wenet/~telechem/ |
| Western Technology Martketing | http://www.westcmtechnology.com/ |

| Robotics | |
| --- | --- |
| Galil | http://galilmc.com/ |
| Parker-Compumotor | http://www.compumotor.com/ |
| Parker-Daedal | http://www.daedalpositioning.com/ |

Regulatory Genes

Genes can include one or more regulatory elements. Some regulatory elements may act to enhance expression; others to inhibit or repress expression. Many regulatory elements are known. Examples include Osmotic response element (ORE); Retinoic acid response element (RARE); Conserved proximal sequence element (PSE); Vitamin D response element (VDRE); Sterol response element (SRE); TNF-alpha)-response element; Peroxisome proliferator response element (PPRE); Abscisic acid-response element (ABRE); Serum response element (SRE); cAMP response element; Antioxidant response element (ARE); Glucocorticoid response element (GRE); Glucocorticoid modulatory element (GME); Gonadotropin-releasing hormone-responsive element (GnRH-RE); Pheromone response element (PRE); Insulin response element (IRE); Interferon consensus response element (ICRE); Estrogen response element (ERE); Hypoxia response element (HRE); E2F transcription factor; Xenobiotic response element (XER); Endoplasmic reticulum stress response element (ERSER); Iron-response element (IRE); Androgen response element (ARE); Stress response element (STRE); RAS-responsive element binding protein 1 (RREB1); and Transforming growth factor, beta-1 response element.

Housekeeping Genes

Housekeeping genes are used to normalize results of expression. These are genes that are selected based on the relatively invariable levels of expression in the system which is being examined, for example, the state such as age or a particular disease. Representative housekeeping genes are shown in Table 2. These include tyrosine 3-monooxygenase/tryptophan 5-monooxygenase activation protein, hypoxanthine phosphoribosyltransferase I (Lesh-Nyhan syndrome), Major histocompatibility complex, class I, C, Ubiquitin C, Glyceraldehyde-3-phosphate dehydrogenase, Human mRNA fragment encoding cytoplasmic actin, 60S Ribosomal protein L13A, and Aldolase C.

Primers and Isolation of Amplicons

In the preferred embodiment, a set of primers for use in detecting changes in expression of genes include the regulatory sequence, are selected based on a protocol such as the one described in detail in Example 1. This process utilizes one or more databases of known genes. The primers are selected to have low levels of homology or sequence identity with other genes and a low frequency of repeats. The preferred primers are between 480 and 700 base pairs length, have a melting point between 75 and 85° C., and include non-consensus sequence with protein coding sequence, so that there is no detectable hybridization between homologous genes, more preferably where there is no hybridization between homologous genes.

The primers are then added to a sample library, for example, obtained from cells from an individual with a particular disease, or of a particular age, or a cell culture, for example, a fibroblast cell culture exposed to a specific set of conditions, such as so many days in space under conditions of no gravity, and polymerase chain reaction or other means of hybridization and amplification performed, to produce specific cDNA fragments hybridizing to the primers, referred to herein as an amplicon or regulatory gene cDNA fragment. These amplicons are then bound at discrete locations on a solid support to form a microarray.

Labels for Probes and Detection

Microarrays typically contain at separate sites nanomolar (less than picogram) quantities of individual genes, cDNAs, or ESTs on a substrate such as a nitrocellulose or silicon plate, or photolithographically prepared glass substrate. The arrays are hybridized to cDNA probes using standard techniques with gene-specific primer mixes. The nucleic acid to be analyzed—the target—is isolated, amplified and labeled, typically with a fluorescent reporter group, radiolabel or phosphorous label probe. After the hybridization reaction is completed, the array is inserted into the scanner, where patterns of hybridization are detected. The hybridization data are collected as light emitted from the reporter groups already incorporated into the target, which is now bound to the probe array. Probes that perfectly match the target generally produce stronger signals than those that have mismatches. Since the sequence and position of each probe on the array are known, by complementarity, the identity of the target nucleic acid applied to the probe array can be determined. There are a variety of labels that are used. cDNAs and ESTs can be detected by autoradiography or phosphorimaging ($^{32}$P). Fluorescent dyes are also used, and are commercially available from suppliers such as Clontech. In the preferred embodiment the label is digoxigenin (DIG). This specific enzymatic labeling probe allows the end result of detecting hybridization reaction intensity by calorimetric evaluation of alkaline phosphatase-coupled antibody to DIG. The enzymatic deposit on each locus of the E-box microarray can be readily analyzed by an upright microscope attached to a CCD camera, without the problem of the long delay needed for exposure time with radioactive probes, or the photobleaching and high background reaction problem associated with the fluorescent probe approach.

Methods for Making Microarrays

The process for making microarrays is shown in FIG. 1. In brief, producing every regulatory sequence-based DNA microarray involves four consecutive steps:

Step 1: Selecting genes bearing a particular regulatory element in their non-coding regions, or genes whose products can bind to a designated regulatory sequence element;

Step 2. Selecting a pair of primer sequences flanking the specific sequence regions of the above two categories of genes, that are unique to the designated gene and heterologous to each other in the specific family of genes;

Step 3. Using the selected primers in PCR reaction to produce amplicons for the specific genes; and Step 4. Printing all the amplicons of selected genes on the same nylon membrane-based microarrays.

Microarrays have been made using this process for human and mouse E2F genes, human antioxidative responsive (ARE) elements, and mouse estrogen-response element (ERE) genes. Other microarrays are in progress, including the human estrogen-response element genes, as well as mouse and human ARE genes.

Diseases and States

The changes in expression of the regulatory genes described herein can be used to assess changes associated with a particular state or disease. Changes in expression of individual genes, either by turning expression on or off, or altering the amount of expression, can be used to assess changes in states such as age or diseases associated with cancer of tissues such as breast, prostate, and colon, immunological changes such as inflammation, neurodegenerative diseases, cardiovascular disorders, and musculoskeletal disorders, including disorders and diseases of bones such as osteoarthritis and osteoporosis, and muscle degeneration.

1% of the Human Genome Sequence is coding sequence; the other 99% is of unknown function. In contrast to the popular belief that these areas are just filling space, and possess no significant impact on total genetic make-up, some portion of them must be regulatory sequences. Therefore, the regulatory sequence-based designer gene approach increases the probability of identifying culprit genes leading to disease evolution.

Diseases, such as cancer, neurodegeneration, and type II diabetes evolve by accumulation of complex traits, combining genetic risk factors with environmental insults. Therefore, knowing a few controlling master genes is an added advantage in diagnosis, prognosis, and therapeutic treatment in determining how such a complex disease evolution occurs, and designing countermeasures to these diseases by a prospective approach, before symptoms ever develop, rather than the current reactive approach, when damage has developed beyond curable status.

Figure 2:
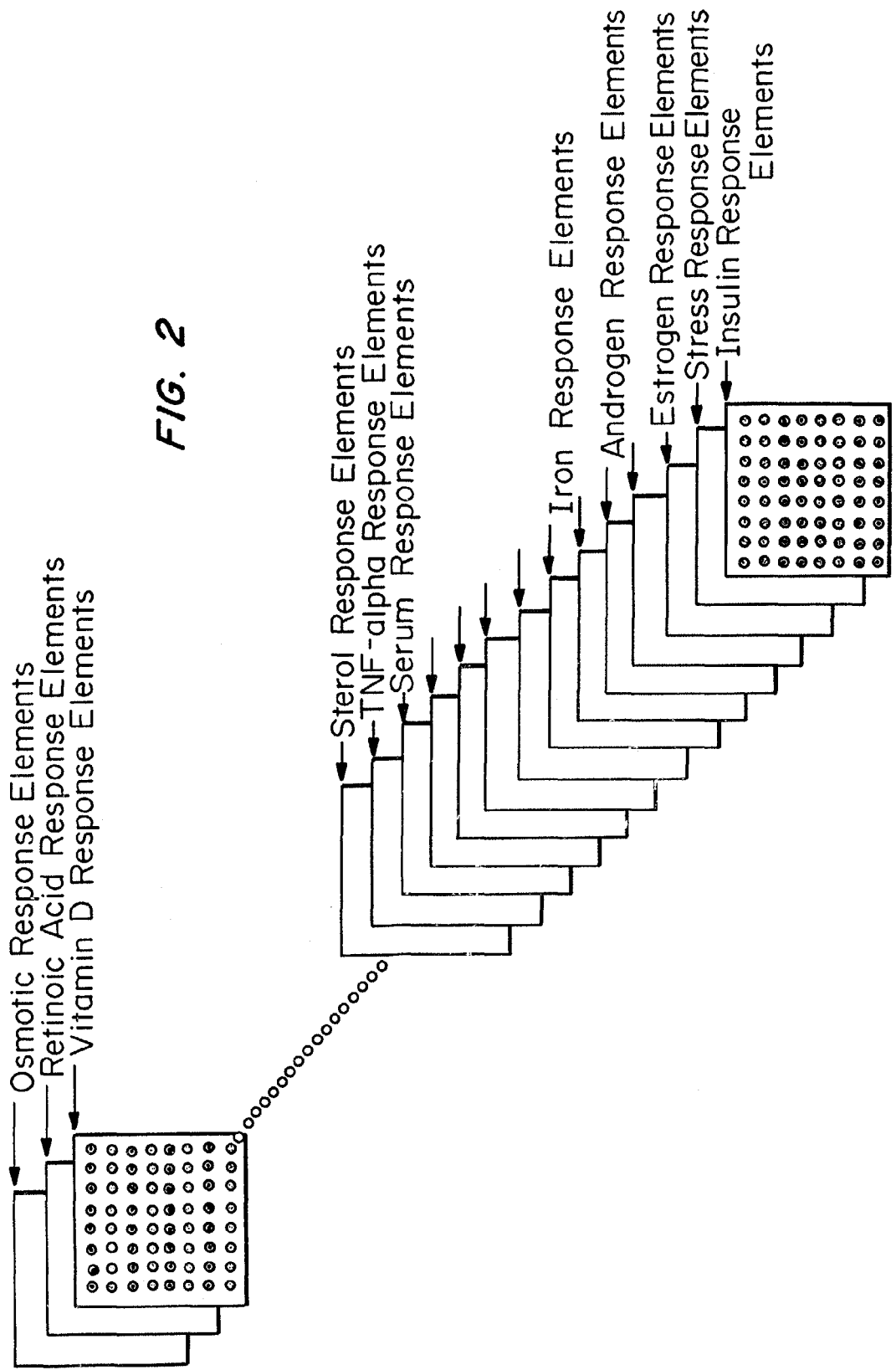
FIG. 2 is a schematic illustrating the number of different microarrays based on the inclusion of specific regulatory elements.

The frequent co-morbidity among the elderly requires the cassette gene screening approach to know how many pathways are involved in disease development. Most elderly patients suffer from multiple disorders, such as cardiovascular problems as well as osteoporosis or neurodegeneration. Most notably, the vascular type of dementia requires gene screening tests of pathways leading to cardiovascular disorders, as well as neurodegeneration. Therefore, selecting a cassette of regulatory gene microarrays provides fast and accurate diagnostic and prognostic assays. A representative cassette is shown in FIG. 2.

In the preferred embodiment, two different types of regulatory sequence-based designer gene microarrays, preferably, human and mouse regulatory sequence-based DNA microarrays, are prepared. The human series is immediately applicable to test human samples for biomarkers for disease profiles; the mouse series is useful in animal studies, where disease treatment efficacy is largely based before human phase I studies can ever be initiated.

The microarrays can be used either in combination of several or singly for gene screening, for gene signaturing to define risk factors and disease states. For example, these gene microarrays can be used for tumor staging for diagnostic and prognostic purposes, or as biomarkers to define the efficacy of chemotherapy or gene therapy treatment. Gene signature profiles based on the use of our regulatory sequence-based designer microarrays provide a fast track to drug discovery, since they provide immediate answers as to which cellular pathways are altered by a disease or corrected by a treatment. The combination of the cassette of designer microarrays can be used for diagnostic, prognostic, or drug-discovery purposes in the following diseases:

a. Neurological disorders: Alzheimer's disease, Parkinson's disease, Huntington's disease
b. Cardiovascular disorders: Myocardial hypertrophy, atherosclerosis, myocardial infarction
c. Bone and Muscle disorders: osteoarthritis, osteoporosis
d. Blood/circulation related disorders: systemic lupus and other autoimmune disorders
e. Cancers: breast cancer, prostatic hypertrophy, prostatic cancer, colon cancer, chronic lymphocytic leukemia, acute lymphocytic leukemia, brain tumors, pancreatic cancer, hepatoma, and so on.

Screening

The arrays can be tested by screening with labeled probes to determine if there is expression of a particular gene in the array and how much, to thereby construct a "fingerprint" of the disease or disorder at that time, using genes present in cells or tissues obtained from one or more individuals having the disease or disorder or characterized by a particular state, such as age. The effect of a compound or composition on the disorder or disease or state can also be assessed by comparing the fingerprint obtained with control cells or tissues, and cells or tissues treated with the compound or obtained from an animal treated with the compound (or compounds, or dosage regime, or exposed to particular conditions). This is especially useful for initial screening of the effect of potential drugs, either to determine potential efficacy and/or toxicity. Those compounds which appear promising can then be further screened to determine if they can reduce or reverse the severity of the disease or disorder. Compounds to be screened can be proteins or peptides, sugars or polysaccharides, nucleic acid molecules, or synthetic molecules.

The present invention will be further understood by reference to the following non-limiting examples.

EXAMPLE 1

Selection of Primers

Define the Project

Search literature, databases, and other contacts for genes and key words to determine the core element of the target genes in the species of interest. Using the above information, locate several different 8–15 base sequences containing the core element from several genes. It is possible to make use of genes from various species.

Turn on the Computer.

Open Internet Explorer and go to TargetFinder (http://hercules.tigem.it/TargetFinder.html). Check "promoter", "TATA", "CAAT", and possibly "enhancer" and "5'UTR" if finding genes is difficult. Scroll down and select specifies, core similarity (usually 1.0), matrix similarity (>0.85), and designate "both strands". All other parameters remain at default values.

Enter chosen sequences in the box according to the following IG format:

;
seq1
ATCTTTGTT1
;
seq2
ATCATTCCC1
;
seq3
GTCACTCTA1

Enter your e-mail address to receive the results, which will probably take overnight. When you receive your results, go to edit and select "Find". Enter part of the known core element sequence and visually search for the second part (e.g., core element=RTGACNNNGC [SEQ ID NO:1], enter TGAC and visually search for GC 3 bases away).

Analyze the Matches Meeting the Above Requirements for the Following:

A. Position of element—must be within the target feature, or within approximately 1000 bases from the target feature.

| Feature: | promoter | (1..1976) |
|---|---|---|
| ID | AF029342 | standard; DNA; HUM; 2056 BP. |
| DT | 08-APR-1998 | (Rel. 55, Created) |
| DT | 08-APR-1998 | (Rel. 55, Last updated, Version 1) |
| DE | Homo sapiens growth hormone-releasing hormone receptor | |
| DE | gene, promoter region. | |
| KW | | |

| matrix name | matrix position (str) | core simil. | matrix simil. | sequence |
|---|---|---|---|---|
| /tmp/bigbox | 1094 (+) | 1.000 | 0.940 | taaaaGTGAccaggca |

In the example above, the matrix position of the element is located within the promoter region.

B. core similarity should be >0.95, and the matrix similarity should be >0.85.
C. sequence—try to avoid repeats and strings of bases.
D. size of target feature—should be >400 bases, but <5000.

Copy and paste the chosen matches (those that fulfill the above parameters) to a "match" file in a word processing program such as Word or WordPerfect. Open windows for the following web sites:

GenBank (http://www.ncbi.nlm.nih.gov/)
UniGene (http://www.ncbi.nlm.nih.gov/blast/blast)
BLAST Search (http://www.ncbi.nih.gov/blast/blast)
Primer 3 Input (http://www.genome.wi.mit.edu/cgi-bin/primer/primer 3 www.cgi)

Copy ID number from Target Finder and paste in GenBank and click on "GO". The gene corresponding to the ID number will be identified by the GenBank accession number. Click on the accession number to reveal details about the gene (scroll down and locate the target region/s to confirm the correctness of your choice). Scroll up and click on the GenBank drop-down menu. Click on FASTA and display. (The FASTA format facilitates subsequent searches.) If the ID number is not recognized by GenBank, try submitting it to EMBL (http://www.embl.org). Open EMBL and past the ID number in the window and click on "FIND". Click on "EMBL DNA Database", and then "ACCESS". Next click on "Simple sequence retrieval" and paste the ID number in the box and hit "enter". Copy the accession number and paste in GenBank, click on "GO" and continue. If this search is not productive, try submitting the ID number to SWISSPROT (http://www.ebi.ac.uk/swissprot/), choose nucleotide in the dropdown menu, and "enter". If this does not produce an accession number, copy the description of the gene (may require the whole description or just partial description to get a result) and paste in GenBank and click on "GO". If this does not produce an accession number, paste the match sequence in BLAST, click "Search". then "Format results", check alignments for the gene of interest, and proceed with the accession number.

Copy the accession number and paste in UniGene. If there are 0 records for the query, proceed with the original accession number. If there are 1 or more records for the query, continue with each of these accession numbers as well as the original. Copy the whole gene sequence and paste in BLAST Search. Scroll down and select the desired organism. Scroll up and click on "Search". Click on "Format results" and wait for BLAST search results to be displayed.

Scroll down to locate the color key for alignment scores. A short description of each alignment sequence will be displayed at the top of the frame as you scroll down the alignments with the cursor arrow. Continue scrolling down the page until you find an mRNA alignment of your gene. Click on the accession number and check the propriety of the mRNA sequence using the same parameters as before (size, location, etc.). Copy the FASTA sequence and paste in Primer3.

Scroll down to "Product Size" and select "OPT:" of 450 (never <400 or >500). Scroll down to "Primer Size" and select "OPT:" of 450 (never <20 or >25). At "Product Tm", enter 75 (Min:), 80 (Opt:), and 95 (Max:). Scroll down to "GC Clamp" and enter "2". At this point, all other parameters remain at default values.

Scroll down and click on "Pick Primers". An example of "Primer3 Output" follows:

| OLIGO | start | len | tm | gc % | any | 3' | seq |
|---|---|---|---|---|---|---|---|
| LEFT PRIMER | 1030 | 22 | 60 28 | 50 00 | 6 00 | 0 00 | CTCTCCAAGTCGACACTTTTCC |
| SEQUENCE SIXE 1617 | | | | | | | |
| INCLUDED REGION SIZE 1617 | | | | | | | |
| PRODUCT SIZE 452, | PAIR ANY COMPL 6 00, PAIR 3' COMPL 2 00 | | | | | | |
| PRODUCT Tm 83 0666 | PRODUCT Tm - min (OLIGO Tm) 22 8601 | | | | | | |
| 1 | AGCAGCCAAGGCTTACTGAGGCTGGTGGAGGGAGCCACTGCTGGGCTCACCATGGACCGC | | | | | | |
| 61 | CGGATGTGGGGGGCCCACGTCTTCTGCGTGTTGAGCCCGTTACCGACCGTATTGGGCCAC | | | | | | |

*Notice the frequency of repeats in this sequence. It is probably not a good candidate for consideration!

Find Alignments

Scroll down to arrows designating the left primer and highlight the sequence starting with the left primer through the designated right primer. Copy and paste in BLAST and click on "search". Click on "Format results" and wait. The goal now is to find significant alignments to the target gene without significant alignments to other genes or clones. Alignments for which the scores are <50 are usually acceptable, as long as they are not too numerous. Alignments with higher scores need to be eliminated by adjusting parameters in Primer3. Go back to Primer3 Output. Scroll down past the sequence and check the "additional oligo" list for sequences located at other positions. Highlight and copy potential sequences and paste in BLAST. Continue as before. If this does not produce satisfactory results, go back to Primer3 and adjust the selection parameters. Start by decreasing the "Product Size-Opt:" to 400 and/or decreasing the "Primer Size-Opt:" to 20. Check alignment scores. If high-scoring alignments have not been eliminated, restrict the size of the available sequence for priming by designating position and length in the "Included Region" box (read the instructions on the right) located below the "Pick Primers" box. Manipulation of the above choices and parameters will eventually result in a few alignments of the same gene with scores >200, perhaps 1 or 2 shorter alignments with scores >80, and a number of short, low-scoring fragments. Avoid alignments which display non-random low-scoring fragments.

Copy and paste the accession number and description of the gene to another word processing file. Go back to Primer3 Output and highlight, copy, and paste the oligo information, including Primer Size and Primer Tm, below the accession number and description.

Go to your "match" file and proceed with the next selection.

What is claimed is:

1. A method for screening for genes whose expression is altered by disease, age, or exogenous agent, comprising:

screening a sample microarray comprising genes from a library, cells or animal exposed to the disease, age or exogenous agent, wherein expression of all of the genes is under control of the same regulatory element, which regulatory element contains defined nucleotide bases to which an enhancer or a repressor may bind;

comparing the expression of the genes to expression of control genes from a library, cells or animal not exposed to the disease, age or exogenous agent; and identifying genes whose expression is altered by the disease, age or exogenous agent.

2. A method for screening for genes whose expression is altered by disease, age, or exogenous agent, comprising:

screening a sample microarray comprising genes from a library, cells or animal exposed to the disease, age or exogenous agent, wherein expression of all of the genes is under control of the same regulatory element;

comparing the expression of the genes to expression of control genes from a library, cells or animal not exposed to the disease, age or exogenous agent; and identifying genes whose expression is altered by the disease, age or exogenous agent;

wherein the microarray further comprises other control genes that are not under the control of the same regulatory element.

3. A method for screening for genes whose expression is altered by disease, age, or exogenous agent, comprising:
screening a sample microarray comprising genes from a library, cells or animal exposed to the disease, age or exogenous agent, wherein expression of all of the genes is under control of the same regulatory element;
comparing the expression of the genes to expression of control genes from a library, cells or animal not exposed to the disease, age or exogenous agent; and
identifying genes whose expression is altered by the disease, age or exogenous agent;
wherein the regulatory element is selected from the group of regulatory elements consisting of osmotic response element, retinoic acid response element, conserved proximal sequence element, vitamin D response element, sterol response element, TNF-alpha response element, serum response element, cAMP response element, antioxidant response element, glucotocorticoid modulatory element, gonadotropin-releasing hormone-response element, pheromone response element, insulin response element, interferon consensus response element, estrogen response element, hypoxia response element, E2F transcription factor, xenobiotic response element, endoplasmic reticulum stress response element, iron-response element, androgen response element, stress response element, RAS-responsive element binding protein 1, and transforming growth factor, beta-1 response element.

4. The method of claim 1 wherein the disease is selected from the group consisting of neurological disorders, cardiovascular disorders, bone and muscle disorders, blood or circulation related disorders, and cancer.

5. The method of claim 4 wherein the diseases are selected from the group consisting of Alzheimer's disease, Parkinson's disease, Huntington's disease, myocardial hypertrophy, atherosclerosis, myocardial infarction, osteoarthritis, osteoporosis, and autoimmune disorders.

6. The method of claim 4 wherein the cancers are selected from the group consisting of breast cancer, prostatic hypertrophy, prostatic cancer, colon cancer, chronic lymphocytic leukemia, acute lymphocytic leukemia, brain tumors, pancreatic cancer, and heptatomas.

7. The method of claim 1 wherein the exogenous agent is a drug or toxin.

8. The method of claim 1 wherein the library is derived from cells or tissues treated with one or more compounds in vitro.

9. The method of claim 1 wherein the library is derived from cells obtained from an individual of a particular age, having a particular disease or disorder, or derived from the neurological system, the cardiovascular system, the musculoskeletal system, or cancerous tissues.

10. The method of claim 1 wherein the exogenous agent is selected from the group consisting of proteins or peptides, sugars or polysaccharides, nucleic acid molecules, and synthetic molecules.

11. The method of claim 8 wherein the compound is selected from the group consisting of proteins or peptides, sugars or polysaccharides, nucleic acid molecules, and synthetic molecules.

12. The method of claim 2 wherein the disease is selected from the group consisting of neurological disorders, cardiovascular disorders, bone and muscle disorders, blood or circulation related disorders, and cancer.

13. The method of claim 12 wherein the diseases are selected from the group consisting of Alzheimer's disease, Parkinson's disease, Huntington's disease, myocardial hypertrophy, atherosclerosis, myocardial infarction, osteoarthritis, osteoporosis, and autoimmune disorders.

14. The method of claim 12 wherein the cancers are selected from the group consisting of breast cancer, prostatic hypertrophy, prostatic cancer, colon cancer, chronic lymphocytic leukemia, acute lymphocytic leukemia, brain tumors, pancreatic cancer, and heptatomas.

15. The method of claim 2 wherein the exogenous agent is a drug or toxin.

16. The method of claim 2 wherein the library is derived from cells or tissues treated with one or more compounds in vitro.

17. The method of claim 2 wherein the library is derived from cells obtained from an individual of a particular age, having a particular disease or disorder, or derived from the neurological system, the cardiovascular system, the musculoskeletal system, or cancerous tissues.

18. The method of claim 2 wherein the exogenous agent is selected from the group consisting of proteins or peptides, sugars or polysaccharides, nucleic acid molecules, and synthetic molecules.

19. The method of claim 2 wherein the compound is selected from the group consisting of proteins or peptides, sugars or polysaccharides, nucleic acid molecules, and synthetic molecules.

* * * * *

SEQUENCE LISTING

```
<160> NUMBER OF SEQ ID NOS: 4

<210> SEQ ID NO 1
<211> LENGTH: 10
<212> TYPE: DNA
<213> ORGANISM: Artificial Sequence
<220> FEATURE:
<221> NAME/KEY: misc_feature
<222> LOCATION: (1)
<223> OTHER INFORMATION: Nucleotide 1 represents miscellaneous core
      element nucleotides
<221> NAME/KEY: misc_feature
<222> LOCATION: (6)..(8)
<223> OTHER INFORMATION: Nucleotides 6 through 8 can be any nucleotide
<223> OTHER INFORMATION: Description of Artificial Sequence: core
      element sequence

<400> SEQUENCE: 1 ntgacnnngc                                                              10

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 2
taaaagtgac caggca                                                       16

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 3
ctctccaagt cgacactttt cc                                                22

<210> SEQ ID NO 4
<211> LENGTH: 120
<212> TYPE: DNA
<213> ORGANISM: Artificial Sequence
<220> FEATURE:
<223> OTHER INFORMATION: Description of Artificial Sequence: primer

<400> SEQUENCE: 4
agcagccaag gcttactgag gctggtggag ggagccactg ctgggctcac catggaccgc       60
cggatgtggg gggcccacgt cttctgcgtg ttgagcccgt taccgaccgt attgggccac      120
```